United States Patent
Ramamurthy et al.

(10) Patent No.: US 7,481,577 B2
(45) Date of Patent: Jan. 27, 2009

(54) ULTRASOUND TRANSDUCER FAULT MEASUREMENT METHOD AND SYSTEM

(75) Inventors: Bhaskar Ramamurthy, Los Altos, CA (US); John Douglas Marshall, Campbell, CA (US); Jan-Ulco Kluiwstra, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 3 days.

(21) Appl. No.: 11/633,956

(22) Filed: Dec. 4, 2006

(65) Prior Publication Data

US 2007/0081576 A1    Apr. 12, 2007

Related U.S. Application Data

(62) Division of application No. 10/679,649, filed on Oct. 6, 2003, now Pat. No. 7,156,551.

(60) Provisional application No. 60/480,910, filed on Jun. 23, 2003.

(51) Int. Cl.
  *G01K 11/22* (2006.01)
  *G01N 25/00* (2006.01)
(52) U.S. Cl. .................... 374/119; 374/117; 374/45
(58) Field of Classification Search ............ 374/117, 374/45, 119
  See application file for complete search history.

(56) References Cited

U.S. PATENT DOCUMENTS

| | | | | |
|---|---|---|---|---|
| 4,469,450 A | * | 9/1984 | DiVincenzo | ............... 374/119 |
| 4,754,760 A | * | 7/1988 | Fukukita et al. | ............ 600/438 |
| 4,936,308 A | | 6/1990 | Fukukita et al. | |
| 4,972,381 A | * | 11/1990 | Mitchell et al. | ............... 367/13 |
| 5,158,087 A | | 10/1992 | Gatzke | |
| 5,297,553 A | | 3/1994 | Sliwa, Jr. et al. | |
| 5,360,268 A | * | 11/1994 | Hayashi et al. | ............. 374/117 |
| 5,370,121 A | | 12/1994 | Reichenberger et al. | |
| 5,410,208 A | | 4/1995 | Walters et al. | |
| 5,624,188 A | * | 4/1997 | West | .......................... 374/119 |
| 5,684,243 A | * | 11/1997 | Gururaja et al. | ............. 73/1.82 |
| 5,771,896 A | | 6/1998 | Sliwa, Jr. et al. | |
| 5,776,065 A | | 7/1998 | Mehmanpazir et al. | |
| 5,788,636 A | * | 8/1998 | Curley | ........................ 600/439 |
| 5,807,269 A | | 9/1998 | Quinn et al. | |
| 5,873,830 A | | 2/1999 | Hossack et al. | |
| 6,142,946 A | * | 11/2000 | Hwang et al. | ............... 600/459 |

(Continued)

*Primary Examiner*—Edward Lefkowitz
*Assistant Examiner*—Mirellys Jagan (57) ABSTRACT

Ultrasound transducer temperatures are measured in response to a temperature dependent property of the ultrasound transducer. The temperature is measured without addition of new electronics or hardware retrofits of the transducer. By implementing software and/or hardware on the ultrasound system rather than the transducer, the temperature is measured in order to provide a level of fault protection. The upgraded or new ultrasound system uses either old or new transducers while still providing temperature measurement. For example, the temperature of the lens or window is measured as a function of changes in attenuation or acoustic velocity. The receive beamformer already implemented on many ultrasound systems is used to measure a temperature dependent property of the lens or window. As another example, the dielectric constant or capacitance of one or more transducer elements is measured using additional hardware in the ultrasound system. The signal line and associated cable for one or more piezoelectric elements is switchably connected between hardware for measuring a capacitance and the receive beamformer for imaging. Rather than temperature, the operational state of the transducer may be diagnosed using acoustic energy response of the lens.

5 Claims, 3 Drawing Sheets

U.S. PATENT DOCUMENTS

| | | |
|---|---|---|
| 6,182,341 B1 | 2/2001 | Talbot et al. |
| 6,270,460 B1 | 8/2001 | McCartan et al. |
| 6,314,380 B1 | 11/2001 | Seip et al. |
| 6,437,487 B1 | 8/2002 | Mohr, III et al. |
| 6,470,286 B1 | 10/2002 | Seip et al. |
| 6,485,430 B1 | 11/2002 | Quinn et al. |
| 6,558,330 B1 | 5/2003 | Ayter et al. |
| 6,575,922 B1 | 6/2003 | Fearnside et al. |
| 6,623,430 B1 * | 9/2003 | Slayton et al. ............... 600/439 |
| 2003/0028113 A1 * | 2/2003 | Gilbert et al. ............... 600/447 |
| 2003/0176789 A1 * | 9/2003 | Kaplan ....................... 600/438 |
| 2003/0204141 A1 * | 10/2003 | Nock et al. .................. 600/439 |
| 2004/0073113 A1 * | 4/2004 | Salgo et al. .................. 600/438 |
| 2004/0102703 A1 * | 5/2004 | Behren et al. ............... 600/443 |
| 2004/0127791 A1 * | 7/2004 | Mast et al. ................... 600/438 |
| 2004/0211240 A1 * | 10/2004 | Gessert et al. ................ 73/1.82 |
| 2004/0267137 A1 * | 12/2004 | Peszynski et al. ........... 600/459 |

\* cited by examiner

ULTRASOUND TRANSDUCER FAULT MEASUREMENT METHOD AND SYSTEM

CROSS-REFERENCE TO RELATED APPLICATION

This application is a divisional of U.S. patent application Ser. No. 10/679,649, filed Oct. 6, 2003, now U.S. Pat. No. 7,156,551.

REFERENCE TO RELATED APPLICATIONS

The present patent document claims the benefit of the filing date under 35 U.S.C. § 119(e) of Provisional U.S. Patent Application Ser. No. 60/480,910, filed Jun. 23, 2003, which is hereby incorporated by reference.

BACKGROUND

The present invention relates to ultrasound transducer temperature or other fault measurement. In particular, an ultrasound transducer temperature or operation is observed for compliance with FDA, UL/IEC or other requirements.

The IEC standards require that an ultrasound transducer temperature not exceed a predetermined limit of 43 deg C. Some ultrasound probes include one or more thermistors added to the stack of the transducer. The thermistors provide a level of fault protection by measuring temperature of the ultrasound transducer and activating a series of protective measures when the temperature reaches a certain value. However, adding thermistors to ultrasound transducer increases the cost of transducers; consequently, most transducers are not built with thermistors. It may be difficult, problematic or impossible to add thermistors to an already existing transducer.

BRIEF SUMMARY

The present invention is defined by the following claims, and nothing in this section should be taken as a limitation on those claims. By way of introduction, the preferred embodiments described below include methods and systems for determining ultrasound transducer temperature by measuring a temperature dependent property of the ultrasound transducer with an ultrasound system. The temperature is measured without addition of new electronics or hardware retrofits of the transducer. By implementing software and/or hardware within the ultrasound system rather than the transducer, an additional level of protection for thermal faults may be realized.

In one embodiment, the temperature of the lens or window is measured as a function of changes in attenuation or velocity of sound. For example, a receive beamformer already implemented on many or all ultrasound systems is used to measure a temperature dependent property of the lens or window. In another embodiment, the dielectric constant or capacitance of one or more transducer elements is measured using additional hardware in the ultrasound system. For example, the signal line and associated cable for one or more piezoelectric elements is connected between hardware for measuring a capacitance and the receive beamformer for imaging.

Transmitting and receiving acoustic energy within the lens or window may alternatively or additionally be used to diagnose transducer operation. Dead elements, delamination or other transducer malfunction is detected based on variation or differences of acoustical energy in the lens or window.

In a first aspect, a method of determining a temperature of an ultrasound transducer is provided. Signals from at least one transduction element of an ultrasound transducer are received. A temperature dependent property of the ultrasound transducer is measured from the received signal. A temperature state of the ultrasound transducer is then determined in response to the measurement.

In a second aspect, a method for determining a temperature of an ultrasound transducer is provided. Elements of an ultrasound transducer are connected with an ultrasound imaging system. A temperature of the ultrasound transducer is measured with components in the ultrasound imaging system. The measurement is made from signals that are on connections also used for acoustic imaging.

In a third aspect, a system for determining a temperature of an ultrasound transducer is provided. The system includes an input operable to connect with a transducer element of the ultrasound transducer. A receive beamformer has a channel connectable to the input. The receive beamformer is operable to output imaging signals in response to a signal on the input. A processor is operable to determine a temperature state of the ultrasound transducer in response to a signal on the input.

Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the Figures, like reference numerals designate corresponding parts throughout the different views.

DETAILED DESCRIPTION OF THE DRAWINGS AND PRESENTLY PREFERRED EMBODIMENTS

Ultrasound transducer temperature measurements are provided for fault protection against thermal faults or other purposes. By using connections between the ultrasound transducer and an ultrasound imaging system also used for ultrasound imaging, the temperature is measured by the ultrasound system without additional hardware or components in the ultrasound transducer. Signals from the ultrasound transducer are used by the ultrasound system to measure a temperature dependent property of the ultrasound transducer. In some embodiments, the dielectric constant of one or more elements is measured to determine the temperature. In other embodiments, the attenuation or acoustic velocity of a transducer lens or window is measured and the temperature of the lens or window is determined. These different embodiments are described below after a general description of the ultrasound system for implementing the embodiments.

Figure 1:
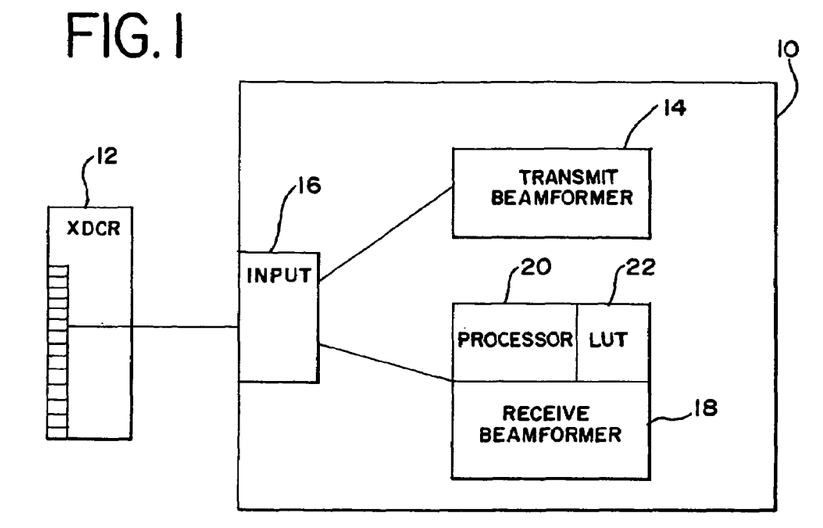
FIG. 1 is a block diagram of one embodiment of an ultrasound system for measuring transducer temperature.

FIG. 1 shows a system 10 for determining a temperature of an ultrasound transducer 12. The measurement or detection of temperature is performed by the system 10 in response to components of the transducer used for acoustic imaging as opposed to sensing the temperature with a thermistor or other temperature measurement specific hardware at the transducer 12.

The transducer 12 comprises a single, one-dimensional, multi-dimensional or other now known or later developed ultrasound transducer. Each element of the transducer 12 is a piezoelectric, microelectromechanical, capacitive membrane ultrasound transducer, or other now known or later developed transduction element for converting between acoustic and electrical energy. Each of the transducer elements connect to a cable, such as a miniaturized coaxial cable, for receiving electrical energy from the ultrasound system 10 and providing electrical energy responsive to acoustic echoes to the ultrasound system 10. In other embodiments, a time division or other multiplex scheme provides signals from two or more elements on a single cable. Wireless connection may also be provided. In yet other alternative embodiments, the transducer 12 is built into the ultrasound system 10, such as ultrasound transducers used in hand-held ultrasound imaging systems. One or more ground connections between the transducer 12 and the ultrasound system 10 are also provided. For example, 128 coaxial cables are provided for a 128 element curved linear array. The center conductors of the coaxial cables each connect to an individual signal electrode of one element while the shields of the coaxial conductors carry the ground connections for their respective elements. Additional coaxial conductors may be included as spares and may also be used to make the ground connection more robust.

The ultrasound system 10 includes a transmit beamformer 14, a transducer input 16, a receive beamformer 18, a processor 20 and a lookup table 22. Additional, different or fewer components may be provided. For example, a detector, scan converter and display are also provided. As another example, a lookup table is not used. The system 10 is a medical diagnostic ultrasound imaging system, such as the Sequoia® or Antares systems manufactured by Siemens Medical Solutions USA, Inc. Imaging includes two-dimensional, three-dimensional, B-mode, Doppler, color flow, spectral Doppler, M-mode or other imaging modalities now known or later developed. Ultrasound systems manufactured by other companies may be used. The ultrasound system 10 is a full size cart mounted system, a smaller portable system, a hand-held system or other now known or later developed ultrasound imaging system.

The transmit beamformer 12 is one or more waveform generators, amplifiers, delays, phase rotators, multipliers, summers, digital-to-analog converters, filters, combinations thereof and other now known or later developed transmit beamformer components. The transmit beamformer 14 is configured into a plurality of channels for generating transmit signals for each element of a transmit aperture. The transmit signals for each elements are delayed and apodized relative to each other for focusing acoustic energy along one or more scan lines. Signals of different amplitudes, frequencies, bandwidths, delays, spectral energy distributions or other characteristics are generated for one or more elements during a transmit event. In one embodiment, 1, 1½ or 2 cycle Gaussian sinusoidal waveforms of 1 to 10 MHz are generated. Square wave or other sinusoidal waveforms at any of various ultrasound frequencies may be generated.

The input 16 is one or both of an electrical connection for switching between transmit and receive events and a physical connection for detachably connecting with an ultrasound transducer 12. The input 16 is operable to connect the ultrasound system 10, the receive beamformer 18 and/or the processor 20 to selectable ones of the transducer elements of the ultrasound transducer 12. For physical connections, the input 16 includes mechanical structure for detachably connecting with the cables of the ultrasound transducer 12. Multi-pin coaxial cable connectors with a screw mount, latch mount, twist mount, or other mounting device for holding the ultrasound transducer cables to the ultrasound system 10 are provided. As a result, a physical connection between the ultrasound system 10 and the transducer 12 is provided.

Electrical connections between transducer elements of the ultrasound transducer 12 and the ultrasound system 10 are also provided by the input 16. In one embodiment, the input 16 is a multiplexer, solid state relays, or high voltage switches for selectable connection between the transmit beamformer 14 and the receive beamformer 18. Additional switches may be provided for connecting the ultrasound transducer elements to other hardware, such as hardware for measuring the temperature. In one embodiment, the input 16 includes a transmit and receive switch. Now known or later developed transmit and receive switches for isolating the receive beamformer 18 from the transmit beamformer 14 during transmit events is provided.

The receive beamformer 18 includes a plurality of channels for separately processing signals received from different elements of the transducer 12. Each channel may include delays, phase rotators, amplifiers, filters, multipliers, summers, analog-to-digital converters, control processors, combinations thereof and other now known or later developed receive beamformer components. The receive beamformer 18 also includes one or more summers for combining signals from different channels into a beamformed signal. A subsequent filter may also be provided. Other now known or later developed receive beamformers may be used. The channels of the receive beamformer 18 are connectable to the input 16, such as through the switches of the input 16. The receive beamformer 16 is operable to output imaging signals in response to signals from the input 16. Electrical signals representing the acoustic echoes from a transmit event are passed through the input 16 to the channels of the receive beamformer 18. The receiver beamformer outputs in-phase and quadrature, radio frequency or other data representing one or more locations in a scanned region. The signals are subsequently detected and used to generate an ultrasound image.

The processor 20 is a control processor, receive beamformer processor, general processor, application specific integrated circuit, digital components, analog components, hardware circuit, combinations thereof and other now known or later developed devices for processing information. The processor 20 is operable to determine a temperature state of the ultrasound transducer in response to a signal from the input 16. For measuring lens or window attenuation or acoustic velocity, the processor 20 connects with the receive beamformer 18, such as being a control processor or processor of the receive beamformer 18. The processor 20 is operable to measure acoustic velocity or attenuation of lens or window of the ultrasound transducer 12 using acoustic signals received at the receive beamformer 18. Signals responsive to an acoustic transmission by the transmit beamformer 14 received from depths associated with the lens or window rather than tissue are isolated by the receive beamformer 18. The processor 20 identifies one or more characteristics of the lens or window echoes for determining an attenuation or velocity of the lens or window. The processor 20 is operable to calculate or determine a temperature of the ultrasound transducer 20 as a function of the attenuation or velocity.

Figure 2:
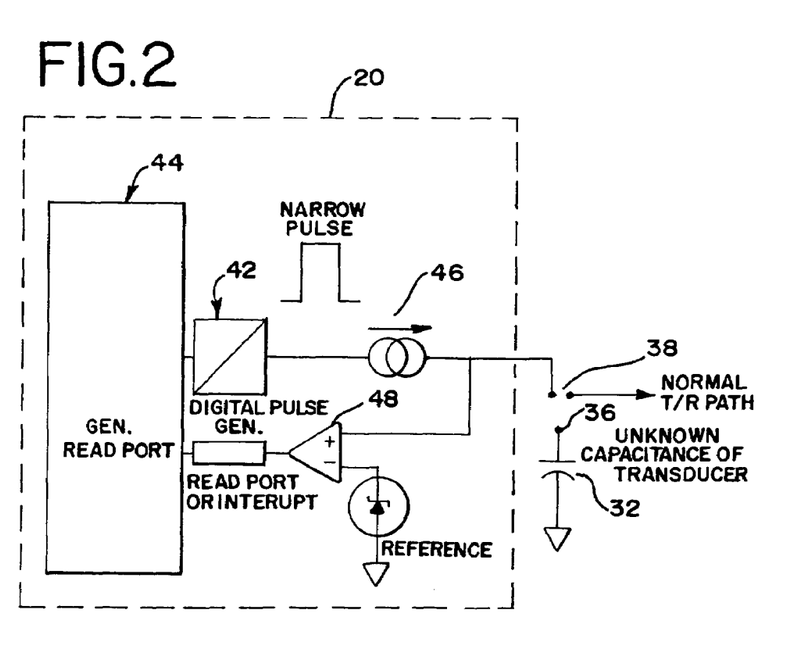
FIG. 2 is a block diagram of one embodiment of a charge pump for measuring dielectric constant.
Figure 3:
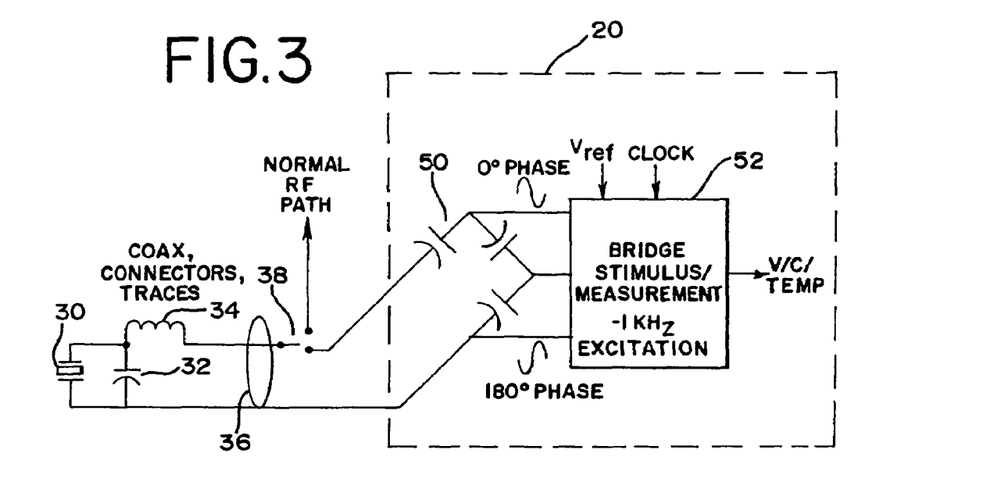
FIG. 3 is a circuit block diagram of one embodiment of a capacitive bridge circuit for measuring dielectric constant.

In another embodiment, the processor 20 includes hardware separate from the receive beamformer 18 for determining the temperature state of the ultrasound transducer 12 in response to signals from the input 16. For example, the processor 20 includes hardware for measuring the dielectric constant. FIGS. 2 and 3 show examples of such hardware for implementing the processor 20. The transducer element 30 includes two electrodes separated by the transduction element. The capacitance of the transduction element varies as a function of the dielectric constant. Due to temperature changes, the dielectric constant and associated capacitance changes. The capacitance is represented by the capacitor 32 and is not precisely known, although the range is limited. An inductance 34 may also be associated with the transducer element 30.

The transducer element 30 and associated capacitance 32 are connected through electrical traces, cables and a connector of the input 16 as represented by 36. A switch 38, such as a switch of the multiplexer of the input 16, is operable to switch the input 16 between the receive beamformer 18 and the processor 20. For example, signals from the input 16 are interleaved between the processor 20 and the receive beamformer 18. The interleaving allows separate imaging and measurement of transducer temperature. The switch 38 acts to isolate the low impedance transmit beamformer 14 and/or receive beamformer 18 from the processor 20. Other switches, such as transistors, relays or other now known or later developed switches may be used. When the switch 38 connects the processor 20 through the input 16 to one or more transducer elements, the transmit and receive beamformers 14 and 18 are disconnected from the transducer element. The connection allows the processor 18 to measure a capacitance of the transducer element connected through the input 16. In alternative embodiments, other mechanisms for isolating the processor 20 from the remainder of the ultrasound system 10 for measuring capacitance or dielectric constant may be used. For example, a capacitive divider or bridge may allow injection of the signals to the transducer element from the processor 20 and measurements without switch 38.

FIG. 2 shows the processor 20 implemented as a charge pump circuit for determining the capacitance 32. The unknown capacitance 32 is determined through the capacitance's ability to hold the charge. Using either the transmit beamformer 14 or a separate digital pulse generator 42 under the control of a processor, discrete components or ASIC 44, one or a plurality of small, quantized charges as represented by the injected charge 46 are applied to the transducer element 30. The resulting voltage across the capacitance 32 is input to a comparator 48, such as a differential comparator. A reference voltage is also input to the comparator 48. The ASIC or processor 44 reads the amplifier output signal. Once the capacitance 32 holds a particular charge (i.e. voltage), the capacitance 32 is determined as a function of the amount of injected charge 46. By variation of the applied charge, which can be varied both in terms of voltage and time, the absolute capacitance is determined by the processor 20. Other charge pumps now known or later developed may be used. In yet another alternative embodiment, an analog-to-digital converter of the receive beamformer 18 is used to quantify the capacitance, such as by determining a DC voltage in response to injection of a known amount of charge. The resulting absolute capacitance or measured capacitance may also include parasitic capacitances from the cable, board traces and tuning elements. Alternatively, a change in capacitance is measured.

FIG. 3 shows an alternative processor 20 with a capacitance bridge 50 and associated processor or ASIC 52. The capacitance bridge 50 includes known capacitance components that are attached to the unknown capacitance 32 as shown through the switch 38. The ASIC 52 generates a low frequency signal relative to the resonant frequency of the element, such a 1 kilohertz signal. Using a 1 kilohertz waveform, many samples are acquired in 100 milliseconds, allowing signal averaging and interleaving of the temperature measurement with imaging transmission and reception. Greater or lesser frequencies may be used. The signal is applied with a 180 degree phase shift to two different points of the bridge 50, such as one to a virtual ground of the element 30 and the other connected through a single known capacitance to the element 30 and associated unknown capacitance 32. When the capacitance 32 of the element 30 matches the capacitance of the bridge 50, a null or zero value signal is provided as an input to the ASIC 52. Variation in the value of the capacitance 32 appears as a small change in the DC or AC amplitude and phase across the output terminals. An analog-to-digital converter in the ASIC 52 measures the change. The change or absolute measure value represents a value of the capacitance 32. In one embodiment, the capacitance bridge 50 is connected to an element not used for imaging, but may be multiplexed or have a selectable connection as discussed above. Other now known or later developed capacitance bridges and associated components may be used in alternative embodiments. The output voltage of the bridge 50 and ASIC 52 is proportional to the capacitance of the element.

In alternative embodiments, other structures and associated processes are used for measuring the dielectric constant or capacitance 32. For example, changes in frequency response, changes in current draw during transmission, or other measurable changes due to differences in capacitance may be used.

In one embodiment, a single processor 20 is used for measuring a temperature of the entire ultrasound transducer 12. For example, the processor 20 connects with an element of a selected position, such as a center, of the array. As another example, the processor 20 is switchably connected with different elements and samples the capacitance associated with different elements at different times. For example, one out of every eight elements is sampled across the face of an array for providing an overall temperature. The capacitances or temperatures are then averaged. Alternatively, a peak temperature or capacitance is selected. As yet another example, the capacitance bridge 50 of FIG. 3 is connected to a plurality of elements. The elements are connected in parallel to provide a better capacitance match between the elements and the capacitance values used in the bridge 50. In alternative embodiments, a plurality of processors 20 is provided for connecting with a respective plurality of elements or groups of elements of the ultrasound transducer 12.

The optional lookup table 12 is a memory, such as a RAM, removable storage media, hard drive or other now known or later developed device for storing data. The lookup table 22 of FIG. 1 outputs a temperature state in response to input information. For example, an attenuation characteristic, an acoustic velocity, a capacitance, a dielectric constant, a voltage, a current, or other temperature dependent characteristic is input to the lookup table 22. The lookup table 22 converts the information to a temperature state. The temperature state includes an actual temperature, the existence of a fault, the lack of a temperature fault or other indicia of the temperature of the ultrasound transducer 12. The lookup table is populated by experiments associating the temperature dependent characteristic measured with actual temperatures. In one embodiment, the lookup table is different for each type of transducer, each individual transducer, the type of transducer construction, one or more materials used in the transducer or other groupings of components having similar temperature relationships. As an alternative to the lookup table, the processor 20 or receive beamformer 18 calculates an actual temperature or the existence of a fault directly using an experimentally determined function.

Figure 4:
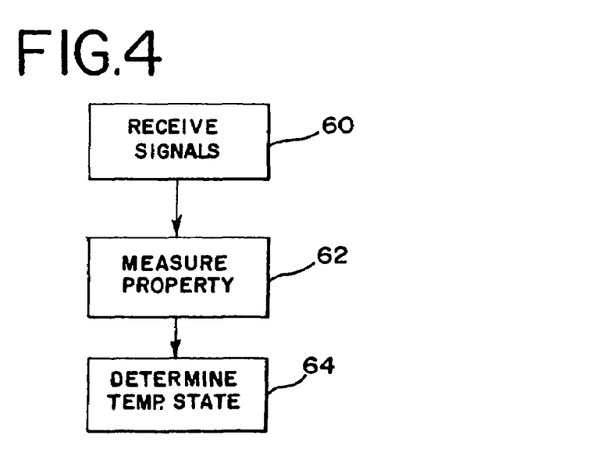
FIG. 4 is a flow chart diagram of one embodiment for determining a temperature state of an ultrasound transducer.

FIG. 4 shows a method for determining a temperature of an ultrasound transducer 12. The temperature of the ultrasound transducers is measured with components in the ultrasound imaging system 10. The signals are measured from connections also used for imaging.

The ultrasound transducer 12 is connected to the ultrasound imaging system 10. Both physical and electrical connections are provided. At least one transduction element is connected electrically to a channel of the receive beamformer 18. Where the transducer 12 includes a plurality of elements, one, a subset or all of the elements are connected in an aperture to the receive beamformer 18 and/or the processor 20.

In act 60 of FIG. 4, signals are received for temperature measurement. The signals are received from one or more transducer elements of the ultrasound transducer 12. The receive signals are associated with measuring a temperature dependent property of the ultrasound transducer. For example, the receive signals represent acoustic echoes, capacitive feedback for a capacitive bridge 50 of FIG. 3, a voltage for the charge injection pump of FIG. 2, or other signal representing a temperature dependent property. In one embodiment, receive signals of act 60 are interleaved with signals received from the same elements of the transducer 12 for ultrasound imaging. Alternatively, one or more characteristics of received signals for ultrasound imaging also provide temperature dependent variations.

In act 62, a temperature dependent property of the ultrasound transducer 12 is measured from the receive signals. For example, components in the ultrasound system 10 are used to measure signals received on connections that are also used for acoustic imaging signals. Alternatively, dedicated connections are provided. Where there are more channels in the system than elements, then the channels not used for imaging at that time may be used to measure temperature. Any of various temperature dependent properties are measured, such as the dielectric constant or lens or window property.

To measure the dielectric constant of one or more transducer elements, the capacitance 32 at the transducer element is measured. A change in the capacitance represents a change in the dielectric constant and associated temperature. The dielectric constant is proportional to temperature. By measuring small changes in the dielectric constant, the temperature may be measured. Certain element materials have greater temperature variations. Transducer material is present in every transducer and indicates an operating temperature of the overall transducer 12. While the external temperature, such as at the surface of the lens or window, is regulated, the transducer element generates the heat. Accordingly, the temperature is measured from the part generating the heat. Inaccuracies due to poor or unknown thermal coupling to remotely located sensors are avoided. The temperature response time may also be more rapid, allowing higher power, low repetition modes to function without damage to the transducers 12.

To measure the dielectric constant or capacitance, one or more transducer elements are switchably connected from the receive beamformer 16 to the temperature measurement circuit of the processor 20. The receive signals are routed to the processor 20 rather than the receive beamformer 18.

By measuring at very low frequencies, such as the 1 kilohertz for the capacitive bridge of FIG. 3 or the narrow pulses for injecting charge of the charge pump of FIG. 2, mechanical and acoustical coupling effects are reduced or excluded. As a result, the temperature is measured while the transducer 12 is operating or coupled with gel to a patient. The use of low frequency information also allows reduction or rejection of free space, radiofrequency effects due to variable amounts of human contact in different environments.

To measure the capacitance, the processor 20 is operable to detect about a 2 pico farad variation. For example, a VF10-5 transducer from Siemens Medical Solutions USA, Inc. has an absolute capacitance value of 450 pico farads. A 20 degree Celsius variation from room temperature to approximately 43 degree Celsius may cause about 2 pico farads of change. The capacitive bridge of FIG. 3 and charge pump of FIG. 2 reduce the effects of cable and other components capacitance as well as provides capacitance information with sufficient resolutions to detect about 0.1 pico farads change. Other resolutions may be used.

Referring to FIG. 2, the temperature dependent capacitances 32 is measured with the charge injection pump of the processor 20 as discussed above. The charge is injected onto at least one transduction element. For example, the charge is injected onto 32 elements equally spaced across a 128 element array. The charge is injected during a sample period repeated about once every 30 to 60 seconds. Greater or smaller intervals may be used. The sample period or measurement is performed for about 100 milliseconds, but greater or lesser periods may be used.

For continuous sampling, a charge is injected and the voltage measured every few milliseconds for a sample period of a few milliseconds. The sample period is interleaved with transmit and receive events. Such interleaving may be conveniently performed by using the transmit beamforming 14 for injecting the charge, and the analog-to-digital converter of the receive beamformer 18 for measuring a resulting voltage, such as where the receive beamformer 18 can measure a DC mode or DC voltage. Where internal rapid heating with a low average temperature is likely or where the transducer is desired to be maintained at a particular temperature, the sample period may occur immediately following application of a transmit and associated receive event. The measurement or sample period is then continuously or intermittently repeated until a sufficient cool down has occurred.

During the sample period, a voltage of each of the transducer elements is determined in response to the injected charge. The injected charge generates a feedback signal or voltage across the elements. By comparing the voltage to the amount of charge injected, the capacitance is measured. In alternative embodiments, the amount of charge injected is varied at different times and the resulting voltages are compared to indicate capacitances. Other now known or later developed charge pump techniques for measuring capacitance may be used.

FIG. 3, as described above, shows measuring a temperature dependent capacitance using a capacitive bridge 50. The sample period and intervals discussed above for the charge pump may be used for the capacitor bridge of FIG. 3. Likewise, the element sampling density discussed above may also be used.

For both the charge pump and the capacitive bridge, the ASICs 44, 52 or other processor receives the voltage or capacitance information and applies the information to the lookup table 22 for determining a temperature. Signals from different elements may be averaged or a peak value identified throughout the set. Other statistical distribution of capacitance, voltage or temperature information may be used.

In another embodiment, the temperature dependent property measure is the lens or window velocity or attenuation. The speed of sound in a lens or window is dependent on temperature. For example, the longitudinal velocity in an RTV lens or window is 1020 meters per second at 20 degrees Celsius, but 974 meters per second at 37 degrees Celsius. By transmitting acoustic energy with the transmit beamformer 14 and receiving echo signals associated with propagation of sound through the lens or window, the velocity is measured. The arrival time of the acoustic echoes is dependent on the lens or window temperature. Measuring arrival time provides an estimate of the lens or window temperature. Different elements are used for transmit than for receive, but a same element may be used for both. Greater lateral propagation through more lens or window material is provided by spacing the receive operative from the transmit operative.

The receive beamformer 18 is configured to isolate or receive signals associated with ultrasound through propagation and echoes from the lens or window. To avoid spurious large peaks due to noise, such as crosstalk, occurring at early times, the receive beamformer 18 is configured to delay 2.5 microseconds or another time from the end of transmit before beginning acquisition. For elements immediately adjacent to a transmit element, the time mask to avoid crosstalk may be shorter, resulting in some additional noise. Alternatively, crosstalk signals are cancelled or masked. Echo signals likely associated with acoustic energy being transmitted through the lens or window into the tissue of a patient and back are also excluded or not received by the receive beamformer 18.

The further a receive element is from a transmit element, the more likely noise occurs in the receive signal. For elements further than about 20 elements from a transmit element, the return signal may be weaker than the noise due to propagation through a longer path. In one embodiment, the receive aperture is limited to a certain number of elements around a transmit aperture. In alternative embodiments, the signal-to-noise ratio is sufficient such that a larger receive aperture may be used. In one embodiment, four or five elements on each side of an element used for transmitting are the receive aperture. For one example embodiment, every tenth element is used for transmitting at different times. Accordingly, a single element transmit aperture is used. Multiple element transmit apertures using either adjacent or sparsely spaced elements may be used. For the receive aperture, five elements on each side of each transmit aperture are used. Adjacent or sparse sampling may be used for any given receive aperture. The receive aperture may also be spaced from the transmit aperture by one or more elements. In yet other embodiments, a single element receive aperture is used.

The transmit and receive apertures are spaced across the face of the array. The temperature is determined for a plurality of locations along the lens or window. The spacing of each transmit and receive operative determines the portion of the lens or window used for measuring velocity.

For each element of the receive aperture, a plurality of signals are received over time. Each signal is associated with a different time or delay after a transmit event. One or more of the signals represents a peak signal envelope of energy propagating through or echoing from within the lens or window. The timing of the peak signal varies as a function of the lens or window velocity. As an alternative to identifying the delay time using the maximum signal, a mean energy (e.g., integrated detected signal), a first arrival of energy over a threshold amount or other function may be used. The time-of-delay for each element is determined for each receive beamformer channel or element of the receive aperture.

Figure 5:
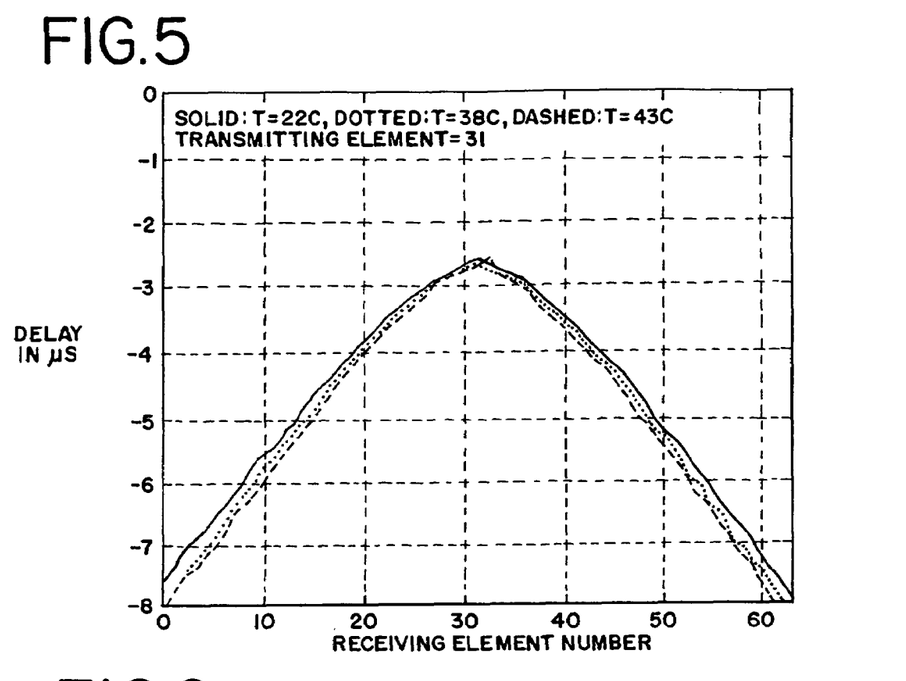
FIG. 5 is a graphical representation of one embodiment showing differences in acoustic velocity of a lens or window as a function of temperature.

FIG. 5 shows a delay in microseconds associated with a 64 element receive aperture and a transmit aperture of the center or 31st element. For each of a plurality of elements, a time of arrival of acoustic energy is determined. As shown in FIG. 5, the time of arrival is provided as a delay in microseconds from the transmit event. Other time of arrival measurements may be provided, such as an amount of time after a transmit event or an amount of time before a final receive event. The delay response time of FIG. 5 is measured using a 5V2c transducer manufactured by Siemens Medical Solutions USA, Inc. The lens or window material is RTV. The delay of interest is identified as the peak signal in each channel. As shown in FIG. 5, the delays were calculated with the transducer lens or window at three different temperatures. The measured delay increases by about 6.5 percent from 24 degrees Celsius to 43 degree Celsius—about 0.3 percent per degree Celsius. This change corresponds closely to the change in longitudinal velocity of sound as a function of temperature. The time-of-arrival is used to estimate the lens or window acoustic velocity and/or lens or window temperature.

The variation in the time-of-arrival is used to calculate or determine temperature. In one embodiment, a lookup table is provided to associate an average, peak or other time-of-arrival value of one or more elements with a velocity or temperature.

In an alternate embodiment, a curved fitting method is used. The variation of the delay for each of a plurality of receive elements away from a single transmitting element in a flat array varies in a predictable fashion given by:

$$t_d = 2/v_1 [t_1^2 + (pn/2)^2]^{1/2}$$

where $t_d$ is the calculated time-of-delay from the transmit event to the received echo signal, $v_1$, is the longitudinal propagation velocity in the lens or window material, $t_1$ is the lens or window thickness, p is the element-to-element pitch and n is the number of element pitches transversed from the transmitting element to the receiving element. The delay, $t_d$, is measured, $t_1$ may be known, and p may be known. As a result, the velocity is calculated. Alternatively, the pitch or thickness may vary or be unknown. Where two or more variables are unknown, any of several curve fitting methods are applied to identify the time-of-delay curve and associated velocity. For example, the pitch is relatively constant but the thickness of the lens or window may vary from transducer to transducer.

Curve fitting effectively averages over the whole data set or the time-of-delay information for multiple receive elements, resulting in suppression of noise. Where one or more values seem particularly noisy or unreliable, the values may be removed from the curve fitting algorithm. For example, a threshold is applied requiring a time-of-delay for each adjacent element within a range of times. The curve fit indicates a velocity of the lens or window. The equation above is provided for a flat array, but curvilinear transducer or arrays with different geometries may also use the same or a similar delay equation. For the same equation, the velocity, thickness and pitch may not be physically correct, but the measured velocity may still indicate expected temperature dependence. The lookup table used for associating the velocity value to temperature may account for any differences in geometry. Alternatively, the equation is altered to account for the differences in geometry.

As another alternative embodiment, a difference for each time of arrival from a known time of arrival profile at a known temperature is used to estimate velocity or temperature. The amount of deviation from the known profile provides an indication of a difference in temperature or velocity. In one embodiment, an averaged difference of all of the elements in the receive aperture from a reference profile is calculated. Signals associated with noise, such signals that deviate from an expected deviation by a threshold amount, may be discarded or masked from the calculation. The fractional difference or percent deviation is then converted to a temperature difference using either a known constant temperature coefficient or an experimentally determined lookup table. An average deviation, peak deviation or other value may be used.

In one embodiment, the delay curve associated with the fault temperature, such as 41 degrees Celsius, is used for the deviation. Curves associated with the delay at other temperatures may be used in alternative embodiments. Multiple curves may be used and the deviation calculated from each of the multiple curves. The velocity determined from each of the referenced curves is then averaged. Other interpolation or extrapolation may be used.

To further reduce noise, responses from several receiving elements are superposed before calculating the time-of-arrival of the envelopes. For example, the same transmit and receive operation is repeated multiple times, and the resulting signals are summed prior to determining the delay. As another example, signals associated with different transmit, different receive or different transmit and receive apertures are summed after phase aligning the signals. For example, acoustic energy is transmitted from a first element and received at a tenth element, and then acoustic energy is transmitted from a second element and received at a tenth element. The receive signals from the tenth element are phased aligned and summed, providing enhanced signal strength relative to the background noise. A single delay value may be determined for multiple elements. Alternatively, a delay profile across multiple elements is determined. The envelope of the composite signal or composite signals across multiple elements is calculated.

Since the phase differences between two elements vary as a function of temperature or lens or window attenuation, an iterative scheme may be used. A typical delay profile is used for the first determination, such as is typical for a type of transducer. The measurement is then repeated by adjusting the phasing for one element relative to another element as a function of the determined velocity. The determined velocity affects the amount of phasing to align the receive signals. The process is repeated until the convergence of the lens or window velocity value or until a lens or window velocity value is within a threshold amount of a previous iteration.

Some transducer lens or window materials acoustically match well to water, gel or tissue. Vary little reflected signal is provided from the lens or window surface for such materials. Transducers constructed with urethane have weak return signals from the lens or window surface. In one embodiment, a lower frequency excitation signal, such as the lowest frequency supported by a transducer, is used to provide a larger reflection from the lens or window surface. As discussed above, multiple transmit and receive firings using the same transmit and receive aperture may be combined by superposing the return signals. The resulting composite signals more likely have a sufficient signal-to-noise ratio. In another embodiment, acoustic energy is transmitted from multiple elements sequentially or one at a time. The receive signals are then shifted and composited. The shift is a phase or delay difference as a function of the number of elements between the two receive apertures. The shifts effectively move the receive aperture laterally by the correct number of elements relative to the transmitting elements. The shifted signals are then summed. For example, acoustic energy is transmitted from a first element and received at a tenth element, and then acoustic energy is transmitted from a second element and received at an eleventh element. The receive signals from the tenth and eleventh elements are summed, providing enhanced signal strength relative to the background noise. Since the delay curve is not altered by this shift, iteration may be avoided.

In yet another alternative to increase the signal-to-noise ratio, acoustic energy is transmitted from multiple elements at a same time. For example, multiple elements are used for transmitting acoustic energy at a same time with their relative delays adjusted so as to create a strong acoustic wavefront in the lens or window focused to a particular receiving element or group of receiving elements. A single data set of received signals is received across the entire array or other subset of the array. Since the delay profile may be unknown due to differences in velocity of sound in the lens or window, multiple iterations are performed as discussed above to determine delays for each element. An approximate delay profile may be estimated based on the lens or window velocity at some nominal temperature. The signal-to-noise ratio is enhanced by using the approximate profile as a starting point for launching an acoustic wave, calculating the lens or window velocity from the summed echoes and then refining the delay profile using the calculated lens or window velocity. The procedure is iterated until the desired precision is achieved. Alternatively, the approximate delay profile may be used without iteration to make a quicker but perhaps rougher estimate of the lens or window velocity.

Figure 6:
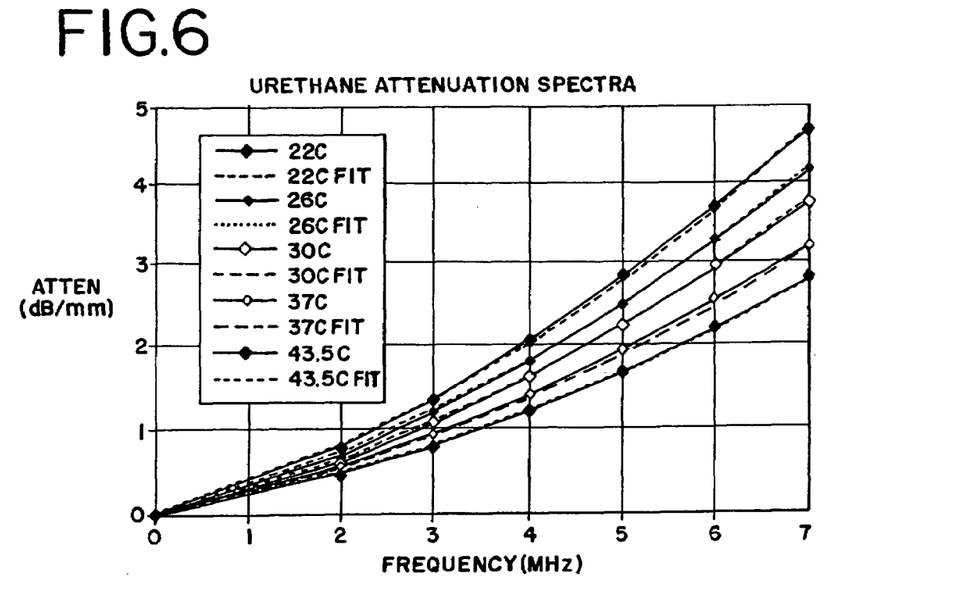
FIG. 6 is a graphical representation of one embodiment of a urethane lens or window attenuation as a function of frequency and temperature.

As yet another alternative, attenuation is used instead or in addition to velocity. Urethane lens or window materials attenuate ultrasonic energy more severely at lower temperatures than higher temperatures, especially at higher frequencies. FIG. 6 shows the attenuation spectra of a urethane lens or window for different temperatures as a function of frequency. The attenuation varies as a function of temperature. The level or amplitude of the return signal from a transmission at a given frequency is measured. For example, the amplitude of a receive signal at one element or a group of elements at a known spacing away from a transmit element is measured at a particular time after the transmit event. The time is selected to be most likely associated with a peak signal, such as amount of delay associated with the time of travel given an assumed velocity. The amplitude level is compared to a reference amplitude.

The measured amplitude is influenced by the reflection coefficient of the lens or window surface, the temperature and any frequency dependent attenuation in the lens or window material. Variations in the lens or window surface reflection coefficient, such as caused by air versus gel or tissue contacting the lens or window, are removed or accounted for by using a curve fitting approach, such as discussed above.

Alternatively, a ratio or difference of signals from two or more elements at varying distance from the transmit element is used to estimate the attenuation of the lens or window material. Since the reflection coefficient is the same for both measurements taken at different times, the ratio value has little or no dependence on the reflection coefficient. Signals from two different elements associated with the same transmission may also be used to determine a ratio. Alternatively, the same or different receive elements are used with a same or different transmit aperture for determining a ratio from amplitudes detected at different times. The receive element is a plurality of elements away from the transmit element, such as 2 to 10 elements. For calculating the ratio from two or more elements at different distances from the transmitting element, the receive elements are spaced 1 to 10 elements apart, but larger spacing may be provided.

In one embodiment, one of the amplitude ratio values is measured at a known temperature, such as a likely room temperature when the transducer is first used in an imaging session. The ratio or changes in the ratio over time indicate temperature or temperature change.

The frequency dependent characteristics of the attenuation are used in another embodiment for determining temperature of the lens or window. Two or more sequential firings are performed at different frequencies. The ratio of the amplitude for receive signals at one element is calculated. Ratios may be calculated for multiple receive aperture elements. The ratio of the amplitude at different frequencies indicates a temperature value or attenuation. A change in attenuation or temperature is calculated by determining a difference in the ratio over time. When one ratio is calculated at a known temperature, the difference indicates an absolute temperature. In alternative embodiments, a single chirp transmission is used, and the decay of the response as the frequency raises during the chirp is measured. The decay represents attenuation and associated temperature.

Since the lens or window temperature may vary across the phase of the transducer 12, the temperature is measured at various locations. For example, a charge pump or capacitive bridge is connected to different elements across the phase of the transducer. As another example, the transmit and/or receive apertures for temperature measurement using lens or window properties are performed across the face of the array. Where a single element is excited and ten neighboring elements receive echo signals, the resulting temperature, attenuation or velocity represents an average temperature in the region prescribed by the 11 elements. By moving the transmit and/or receive elements, a temperature profile across the face of the transducer is measured.

Referring again to FIG. 4, the temperature state is determined in act 64. Using any of the temperature dependent measurements discussed above, the measured value is used to identify a temperature state, such as an actual temperature or a fault condition. For example, a change in a value or an absolute value indicates a temperature above a thermal fault. As a result, the ultrasound system 10 ceases to transmit acoustic energy from the ultrasound transducer 12 until the temperature falls below the thermal fault temperature or another hysteresis temperature. The lookup table 22 or an actual calculation are used to identify a temperature or existence of a fault based on the measured property. In one embodiment, the temperature is output to the user automatically or in response to a user indicated interest in the ultrasound transducer temperature.

In one embodiment, the temperature state is determined for all transducers using the same formulas and/or lookup tables. In alternative embodiments, different lookup tables or formulas are used for different types of transducers. For example, the ultrasound system 10 detects a type of transducer connected or the user indicates via an input device the type of transducer connected. The measured property is compared against a reference property using a lookup table for the type of transducer. Where a variation within an identifiable subset of transducers occurs, a calibration may be provided for particular transducers.

In one embodiment, calibration is performed by taking a measurement at a known temperature. For example, a thermistor or other temperature measurement device is provided in the ultrasound system 10. In alternative embodiments, the known temperature is determined by a user input. For example, the user identifies a temperature from a thermostat or other source of information and inputs the temperature information to the ultrasound system 10. Where the transducer is stored within the room, the temperature of the transducer may be the same as the ambient temperature. In another embodiment, the sonographer verifies that the transducer is at a typical ambient hospital temperature, such as a temperature within a 19 to 23 Celsius range. When a transducer is first used for imaging during a first and/or any subsequent imaging session, the temperature dependent property is measured. The property is calibrated to the known temperature.

As the device is subsequently used, further measurements of the temperature dependent property are performed. Changes in the measurement of the temperature dependent property indicate a change in the transducer temperature. The amount of change associated with the thermal fault is determined experimentally as a function of the type of transducer, the specific, or all transducers.

As the temperature approaches a predetermined value, such as less than a thermal fault, the ultrasound system 10 may perform actions to reduce or maintain the temperature without raising the temperature further. For example, the frame rate is slowed, the amplitude of transmitted energy is decreased, or other actions are taken to reduce the amount of transmitted ultrasound energy over a period. When a thermal fault occurs, the user is notified on the display. The system then ceases operation until the transducer 12 has cooled sufficiently.

In yet another alternative embodiment, the reference measurement of the temperature dependent property and the current temperature of the ultrasound transducer is performed during manufacture of the transducer. The resulting calibration information is either provided to all ultrasound systems, provided for the ultrasound system or systems associated with the purchaser of the transducer or provided with a memory in the transducer 12. For example, a non-volatile memory device, such as an EEPROM, is provided within the transducer 12. Once connected, the transducer 12 communicates the reference measurement information to the ultrasound system 10. The memory device in the transducer 12 may also or alternatively identify the transducer 12 to the ultrasound system 10 where the ultrasound system 10 includes the calibration information in a memory. Alternatively, the user identifies a particular serial number of a transducer connected to the ultrasound system 10.

In the calibrations at the time of manufacture or time of use discussed above, a single temperature measurement is used to calibrate with a single or multiple measurements of the temperature dependent property. In other embodiments, multiple measurements of the temperature dependent property and known temperature of the transducer are performed. For example, multiple measurements are performed at the time of manufacture by heating the transducer to different known temperatures. The measurements of the temperature dependent properties are performed at each of various temperatures, allowing interpolation, extrapolation or determination of functions for indicating an absolute temperature given any measured temperature dependent property for a particular transducer or type of transducer. Other calibration techniques may be used.

Transmitting and receiving acoustic energy within the lens or window may alternatively or additionally be used to diagnose transducer operation. Dead elements, delamination or other transducer malfunction is detected based on variation or differences of acoustical energy in the lens or window. A transducer operation-dependent property of the ultrasound transducer is determined from received acoustic signals. For example, a time-of-arrival is determined for each of a plurality of elements. A lens or window property affected by the state of the transducer is determined from the times-of-arrival. A threshold time or arrival or amount of received energy may indicate a dead element, delamination or other transducer malfunction. By calculating a different from an expected time-of-arrival or acoustic energy profile, one or more different transducer operational states may be determined.

While the invention has been described above by reference to various embodiments, it should be understood that many changes and modifications can be made without departing from the scope of the invention. For example, thermistors or other temperature measurement devices may be provided within a transducer in addition to measurements using devices in the ultrasound system. Dummy elements or connections not used for acoustic imaging may be used for determining the temperature of the ultrasound transducer 12.

It is therefore intended that the foregoing detailed description be regarded as illustrative rather than limiting, and that it be understood that it is the following claims, including all equivalents, that are intended to define the spirit and scope of this invention.

We claim:

1. A method of determining performance or operation of an ultrasound transducer, the method comprising:
   (a) receiving signals from at least one transduction element of the ultrasound transducer;
   (b) determining a transducer operation-dependent property of the ultrasound transducer from the received signals; and
   (c) automatically determining an operation state of the ultrasound transducer in response to determining the transducer operation-dependent property
   wherein (b) comprises determining an acoustic property of a lens or window of the ultrasound transducer, the acoustic property being the transducer operation-dependent property.

2. The method of claim 1 further comprising:
   (d) transmitting acoustic energy with a transmit beamformer;
   wherein (a) comprises receiving the signals responsive to echo signals responsive to (d) and associated with lens or window depths with a receive beamformer.

3. The method of claim 1 wherein (b) comprises:
   (b1) determining, for each of a plurality of elements including the at least one transduction element, a time-of-arrival of acoustic energy represented by the received signals; and
   (b2) estimating a lens or window property, as the acoustic property, from the times-of-arrival.

4. The method of claim 1 wherein (b) comprises:
   (b1) determining, for each of a plurality of elements including the at least one transduction element, a time-of-arrival of acoustic energy represented by the received signals; and
   (b2) calculating a difference for each time of arrival from a time-of-arrival profile for a known profile.

5. A method of determining performance or operation of an ultrasound transducer, the method comprising:
   (a) receiving signals from at least one transduction element of the ultrasound transducer;
   (b) determining a transducer operation-dependent property of the ultrasound transducer from the received signals;
   (c) automatically determining an operation state of the ultrasound transducer in response to determining the transducer operation-dependent property; and
   (d) connecting the ultrasound transducer to an ultrasound imaging system, the connection connecting the at least one transduction element to a receive beamformer channel of the ultrasound imaging system;
   wherein (b) comprises determining the transducer operation-dependent property with components in the ultrasound imaging system, the received signals being received by the ultrasound imaging system on the connections also used for acoustic imaging signals received, from the ultrasound transducer, by the ultrasound imaging system to generate an ultrasound image.

* * * * *